(12) United States Patent
Teunissen

(10) Patent No.: US 10,821,020 B2
(45) Date of Patent: Nov. 3, 2020

(54) FORCED AIR WARMING BLANKET

(71) Applicant: THE SURGICAL COMPANY INTERNATIONAL B.V., Amersfoort (NL)

(72) Inventor: Berend Jan Teunissen, Haaksbergen (NL)

(73) Assignee: THE SURGICAL COMPANY INTERNATIONAL B.V., Amersfoort (NL)

( * ) Notice: Subject to any disclaimer, the term of this patent is extended or adjusted under 35 U.S.C. 154(b) by 718 days.

(21) Appl. No.: 14/592,234

(22) Filed: Jan. 8, 2015

(65) Prior Publication Data
US 2015/0196422 A1  Jul. 16, 2015

(30) Foreign Application Priority Data

Jan. 10, 2014 (EP) .................................... 14150853

(51) Int. Cl.
*A61F 7/00* (2006.01)
*A61F 7/02* (2006.01)

(52) U.S. Cl.
CPC ...... *A61F 7/0097* (2013.01); *A61F 2007/006* (2013.01); *A61F 2007/0091* (2013.01); *A61F 2007/0098* (2013.01); *A61F 2007/0271* (2013.01)

(58) Field of Classification Search
CPC combination set(s) only.
See application file for complete search history.

(56) References Cited

U.S. PATENT DOCUMENTS

| | | |
|---|---|---|
| 5,165,400 A | 11/1992 | Berke |
| 5,674,269 A | 10/1997 | Augustine et al. |
| 6,277,144 B1 | 8/2001 | Tomic-Edgar et al. |
| 6,689,155 B2 | 2/2004 | Gammons et al. |
| 6,699,270 B2 | 3/2004 | Gammons et al. |
| 6,827,729 B2 | 12/2004 | Gammons et al. |
| 7,022,130 B2 | 4/2006 | Gammons et al. |
| 2003/0023289 A1 | 1/2003 | Gammons et al. |
| 2006/0052851 A1* | 3/2006 | Anderson ............. A61F 7/0097 607/104 |
| 2006/0184217 A1* | 8/2006 | Van Duren ........... A61F 7/0097 607/104 |

(Continued)

OTHER PUBLICATIONS

Search Report for EP 14150853.1 dated Jun. 11, 2014.

*Primary Examiner* — Joseph A Stoklosa
*Assistant Examiner* — Adam J Avigan
(74) *Attorney, Agent, or Firm* — Nixon & Vanderhye, P.C.

(57) ABSTRACT

A forced air warming blanket for providing conditioned gas to a patient and a method of using and manufacturing the same. The forced air warming blanket comprises a first blanket portion which comprises a generally U-shaped inflatable region, at least part of the external surface of the inflatable region being air permeable, as well as an inlet port for receiving temperature conditioned gas. An inner blanket portion is provided within the generally U-shaped inflatable region of the first blanket portion. The inner blanket portion is at least partially (or wholly) detachable from the first blanket portion. The inner blanket portion may also have an inflatable region. An outer blanket portion may be provided.

18 Claims, 8 Drawing Sheets

(56) References Cited

U.S. PATENT DOCUMENTS

| | | | |
|---|---|---|---|
| 2008/0053462 A1* | 3/2008 | Teves | A61B 46/00 128/849 |
| 2010/0161012 A1 | 6/2010 | Van Liebergen et al. | |
| 2010/0179624 A1* | 7/2010 | Anderson | A61F 7/00 607/104 |
| 2010/0211141 A1 | 8/2010 | Pierre et al. | |
| 2011/0009930 A1* | 1/2011 | Officier | A61F 7/0097 607/104 |
| 2012/0047623 A1* | 3/2012 | van Oudenallen | A61F 7/02 2/114 |

* cited by examiner

FORCED AIR WARMING BLANKET

This application claims priority to EP 14150853.1 filed Jan. 10, 2014, the entire content of which is hereby incorporated by reference.

FIELD OF THE INVENTION

The present invention relates to the field of forced air warming blankets.

BACKGROUND TO THE INVENTION

Forced air warming blankets are used to regulate the temperature of subjects (e.g. human patients), particularly before, during or after a medical procedure, or to gradually raise the temperature of a patient suffering from hypothermia. They include an air inlet for receiving temperature conditioned air and an air permeable surface out of which temperature conditioned air is forced in use, by virtue of pressure within the forced air warming blanket, across the skin of or around the body of the subject.

Forced air warming blankets are produced in a variety of shapes and sizes, depending on the expected application of the forced air warming blanket. For example, US 2010/0161012 discloses a whole body forced air warming blanket to be placed over a subject and US 2011/0009930 discloses a whole body forced air warming blanket to be placed under a subject, for example during an operation. It is also known to provide forced air warming blankets which cover part of a subject, e.g. the torso, optionally with one or both arms outstretched, or to provide forced air warming blankets to be placed over a subject but having an aperture, e.g. over the chest, to allow surgical access. U.S. Pat. No. 5,165,400 describes a generally U-shaped forced air warming device, allowing surgical access from above a subject while supplying warming conditioned air around the subject.

It is therefore important to use suitable forced air warming blankets during surgical procedures, to allow the necessary access, while maintaining patient temperature. Different forced air warming blankets may be required before or after surgical procedures. Accordingly, it is sometimes necessary to use multiple forced air warming blankets during a treatment procedure, which can lead to waste, or require many types of forced air warming blanket to be stocked.

Furthermore, difficulties can arise if it is necessary to adapt a planned use of forced air warming blankets during a treatment procedure, for example, if patient temperature changes, requiring additional, or less warming, or if there is some uncertainty as to what heating will be required, for example during an emergency operation to treat the victim of a serious accident.

Accordingly, the invention addresses the technical problem of providing a forced air warming blanket which is flexible in the way in which it can be employed, allowing it to be used with multiple types of procedure, or to allow adjustment of temperature management during a procedure.

SUMMARY OF THE INVENTION

According to a first aspect of the invention there is provided a forced air warming blanket for providing conditioned gas to a subject, the forced air warming blanket comprising:
a first blanket portion which comprises a generally U-shaped inflatable region, at least part of the external surface of the inflatable region being air permeable, the inflatable region further comprising an inlet port for receiving temperature conditioned gas; and
an inner blanket portion within the generally U-shaped inflatable region of the first blanket portion;
wherein the inner blanket portion is at least partially detachable from the first blanket portion.

Accordingly, in use, temperature conditioned gas is received into the generally U-shaped inflatable region through the inlet port and is forced out of the generally U-shaped inflatable region through the at least part of the external surface which is air permeable, and thereby conveyed to a subject. A subject can thereby be warmed.

However, temperature conditioned gas may be conveyed to the subject through the generally U-shaped inflatable region with the inner blanket portion attached or at least partially detached (and in some embodiments fully detached) from the generally U-shaped inflatable region. Accordingly, the inner blanket portion can be at least partially detached to allow access to a patient, to the extent required during a particular operation. The at least partial detachment can take place when required. Therefore, the forced air warming blanket might be employed initially with the inner blanket portion fully attached to the first blanket portion, for example before a procedure, and then the inner blanket portion can be at least partially detached at a later stage, for example during a procedure. This can take place while temperature conditioned air continues to be supplied to a subject through the generally U-shaped inflatable region.

This will also mean that the at least partially detached inner blanket portion will be of the right shape to fill any gap left in the forced air warming blanket. It is therefore readily to hand if required for another warming purpose. It could be put back roughly into place, for example at the end of a procedure. Optionally, the inner blanket portion is reattachable to the first blanket portion.

Therefore, the invention provides a forced air warming blanket which can be used flexibly. It may reduce the number of configurations of forced air warming blanket which must be stocked by a hospital to carry out procedures and allows the amount of forced air warming to be varied during a procedure.

The forced air warming blanket can therefore provide the benefits of a generally U-shaped inflatable region, of the type disclosed in U.S. Pat. No. 5,165,400, such as reducing temperature conditioned air from escaping laterally and allowing access for surgeons, with the benefits of blankets extending over or under a subject, and the various parts can be at least partially (or wholly) detached when required.

Typically, the first blanket portion has a generally U-shaped inner edge, bounding the inner blanket portion on at least three sides. Typically, the first blanket portion is generally U-shaped. The generally U-shaped inflatable region typically comprises a first tube portion and an opposed second tube portion, with a cross piece therebetween. The first blanket portion typically comprises a first elongate portion (comprising the first tube portion) and an opposite second elongate portion (comprising the second tube portion) with a connecting portion (comprising the cross piece) extending between one end of the first elongate portion and one end of the second elongate portion. The inner blanket portion typically extends between the first and second elongate portions. The inner blanket portion typically extends from the cross piece. The inner blanket portion typically extends from the cross piece to the opposite ends of the first and second elongate portions.

In some embodiments, the inner blanket portion is entirely detachable from the first inflatable portion. In this case, the inner blanket portion may be removed entirely if required, and optionally discarded. Alternatively, the inner blanket portion can be kept in place while the first blanket portion is removed.

The forced air warming blanket may further comprise an outer blanket portion outside the first blanket portion. The outer blanket portion may extend away (laterally outwards) from the first and second elongate portions. The outer blanket portion may extend away (longitudinally from) the connecting portion. In some embodiments, the outer blanket portion may contact the inner blanket portion (e.g. if the first blanket portion extends beyond the first and second elongate portions).

It may be that the outer blanket portion is at least partially (or wholly) detachable. Again, this means that the product can be used flexibly. It may be that the outer blanket portion can be used to tuck the forced air warming blanket under a bed or mattress.

It may be that the inner blanket portion is not inflatable. However, the inner blanket portion may comprise an (inner) inflatable region. It may be that at least part of the external surface (for example, the majority of, or all of, one side of) the inner inflatable region of the inner blanket portion is air permeable and the inner blanket portion comprises an inlet port for receiving temperature conditioned gas into the (inner) inflatable region. Accordingly, in use, temperature conditioned gas can be received into the inner inflatable region through the inlet port of the inner blanket portion and so be forced out of the inner inflatable region through the at least part of the external surface of the inner inflatable region which is air permeable and thereby conveyed to a subject. Therefore, in such embodiments, the first blanket portion and the inner blanket portion can function as independent forced air warming devices. This is advantageous as a user may decide to warm the patient by supplying temperature conditioned air to the generally U-shaped inflatable region of the first blanket portion, the inflatable region of the inner blanket portion, or to both the generally U-shaped inflatable region of the first blanket portion and the inflatable region of the inner blanket portion, and this may be changed during use. This also facilitates options such as detaching the inner blanket portion from the first blanket portion and using it independently as a forced air warming device.

Typically, the outer blanket portion is not inflatable. However, the outer blanket portion may comprise an (outer) inflatable region. It may be that at least part of the external surface (for example, the majority of, or all of, one side of) the outer inflatable region of the outer blanket portion is air permeable and the outer blanket portion comprises an inlet port for receiving temperature conditioned gas into the (outer) inflatable region. Accordingly, in use, temperature conditioned gas can be received into the outer inflatable region through the inlet port of the outer blanket portion so be forced out of the outer inflatable region through the at least part of the external surface of the outer inflatable region which is air permeable and thereby conveyed to a subject.

The forced air warming blanket may comprise opposed first and second sheets, wherein the first sheet is air impermeable and the second sheet is air permeable, and one or more seals which connect the first and second sheets and thereby define the generally U-shaped inflatable region. The inlet port typically comprises an aperture in the first or second sheet. Therefore, temperature conditioned air can be introduced into the inflatable region (or regions) defined by the first and second sheets, and the said one or more seals, and forced through the second sheet to thereby warm a subject in use. The part of the generally U-shaped inflatable region formed from the second sheet may function as the said at least part of the external surface of the generally U-shaped inflatable region which is air permeable.

The first and/or second sheets may be formed from one or more layers. Where they are formed from more than one layer, the multiple layers may be formed as a laminated structure or with gaps between the layers.

It may be that the inner blanket portion is also formed from the opposed first and second sheets. In embodiments where the inner blanket portion is formed from the opposed first and second sheet and the inner blanket portion is inflatable, one or more further seals may be provided to define the (inner) inflatable region of the inner blanket portion. The part of the inflatable region formed from the second sheet can function as the said at least part of the external surface of the inner inflatable region which is air permeable.

The forced air warming blanket may comprise one or more tear lines (typically perforations) between the first blanket portion and the inner blanket portion, which one or more tear lines can be torn to at least partially (or in some embodiments wholly) detach the inner blanket portion.

The one or more tear lines may be tear lines (typically lines of perforations) extending through the said first and second sheets. One or more tear lines (typically lines of perforations) may be intermediate a first seal between the first and second sheets which defines (at least in part) the first blanket portion and a second seal between the first and second sheets which defines (at least in part) a said inflatable region of the inner blanket portion. The one or more tear lines may extend to the periphery of the forced air warming blanket. A generally U-shaped tear line may separate the first blanket portion and the inner blanket portion.

However, inner blanket portion may comprise only one of the first and second sheets, or the inner blanket portion may be formed from one or more sheets other than the first and second sheets.

It may be that the outer blanket portion is also formed from the opposed first and second sheets. In embodiments where the outer blanket portion is formed from the opposed first and second sheets and the outer blanket portion is inflatable, one or more further seals may be provided to define the (outer) inflatable region of the outer blanket portion. The part of the outer inflatable region formed from the second sheet can function as the said at least part of the external surface of the outer blanket portion which is air permeable.

The forced air warming blanket may comprise tear lines (typically lines of perforations) between the first inflatable portion and the outer blanket portion, which tear lines can be torn to at least partially (or in some embodiments wholly) detach the outer blanket portion. The tear lines may be tear lines (typically lines of perforations) extending through the said first and second sheets.

Again, the tear lines may be tear lines (typically lines of perforations) extending through the said first and second sheets. One or more tear lines (typically lines of perforations) may be intermediate a first seal between the first and second sheets which defines (at least in part) the generally U-shaped inflatable region and a second seal between the first and second sheets which defines (at least in part) a said inflatable region of the outer blanket portion. The one or more said tear lines may extend to the periphery of the forced air warming blanket. A generally U-shaped tear line may separate the outer blanket portion from the first inflatable portion.

However, outer blanket portion may comprise only one of the first and second sheets, or the outer blanket portion may be formed from one or more sheets other than the first and second sheets.

The one or more seals may, for example, be heat seals or welds.

Typically, the forced air warming blanket according to the invention may be used to cover the subject, or to be placed underneath the subject. In either case, the forced air warming blanket is typically deployed with the said air permeable part or parts of the external surface oriented to face the patient. Where the first blanket portion (and in some cases also the inner blanket portion and/or outer blanket portion) is formed from opposed first and second sheets, it is typically deployed with the second (air permeable) sheet facing the patient (i.e. on the lower side when the forced air warming blanket is positioned above the patient and on the upper side when the forced air warming blanket is positioned below the patient).

Typically, the inlet port is part of the cross piece of the generally U-shaped inflatable region. However, the inlet port may be part of the first tube portion or the second tube portion.

The generally U-shaped inflatable region may comprise a single continuous chamber that extends through the first and second elongate portions and the connecting portion (for example, the first tube portion, second tube portion and cross-piece may together form a single generally U-shaped chamber).

However, the generally U-shaped inflatable region may comprise a plurality of chambers. The chambers may be in fluid communication with each other such that temperature conditioned gas may pass between them.

Typically, the first and second tubes are elongate and parallel to each other. The cross piece may extend between the ends of the first and second tubes.

Preferably, the generally U-shaped inflatable region extends across and along either side of the subject during use. Typically, the head of the subject extends beyond the forced air warming blanket from the end opposite the cross piece of the U-shaped inflatable region. The first tube portion of the generally U-shaped inflatable region may extend along one side of the patient. The second tube portion of the generally U-shaped inflatable region may extend along the other, opposed side of the patient. The cross piece of the generally U-shaped inflatable region may be proximate to the feet of the patient. Accordingly, the generally U-shaped inflatable region may at least partially retain temperature conditioned gas between itself and the patient.

In embodiments where the forced air warming blanket is suitable to be placed over the patient, the outer blanket portion may extend the reach of the conditioned gas flow of the forced air warming blanket. For example, the outer blanket portion may retain conditioned gas between the bed a patient is lying upon and the outer blanket portion.

In embodiments where the forced air warming blanket is suitable to be placed underneath the patient, the outer blanket portion may secure the forced air warming blanket to the bed of the patient. For example, the outer blanket portion may be tucked into the bed or under the mattress upon which a patient is lying.

The second sheet may be multi-laminar. The second sheet may comprise an inward air-permeable layer and an outward air-permeable layer, where the inner layer has greater resistance to the flow of air to distribute air flow across the second sheet.

The second sheet may have an air permeability of 1-400 mm/s measured at a pressure drop of 100 Pa. It may be that the air-permeability of the second sheet is less than 300 mm/s, or less than 200 mm/s. The resulting low velocity of air coming from the second sheet counteracts any draught effects when this air flows along the patient. Typically, the air permeability of the air-permeable material of the second sheet balances heat transfer performance of the material and air resistance.

Preferably, the forced air warming blanket is disposable. As such, the forced air warming blanket is clean and sterile before use, without the costs associated with cleaning and sterilising used forced air warming blankets. Alternatively, the forced air warming blanket may be re-usable.

The invention extends in a second aspect to a method of manufacturing a forced air warming blanket comprising the steps of:

bringing a first sheet of an air-impermeable material and a second sheet of an air-permeable material into contact; and forming one or more seals between the first sheet and the second sheet and forming one or more tear lines through the first and second sheets to thereby form a forced air warming blanket according to the first aspect of the invention.

The method of the present aspect provides a cheap and simple way of manufacturing a forced air warming blanket according to the first aspect of the invention.

The one or more seals thereby define the generally U-shaped inflatable region, the inner inflatable region (where present) and the outer inflatable region (where present).

The step of forming connections between the first and second sheets may define an outer blanket portion. The method may comprise the step of perforating the first and second sheets along the connection that separates the first blanket portion from the outer blanket portion, such that the outer blanket portion is at least partially detachable.

According to a third aspect of the invention, there is provided a method of using a forced air warming blanket according to the first aspect of the invention, comprising arranging the forced air warming blanket above or under a subject, introducing conditioned air into the generally U-shaped inflatable region through the inlet of the generally U-shaped inflatable region, and at least partially (or fully) detaching the inner blanket portion.

The inner blanket portion may be at least partially (or fully) detached before, after or while conditioned air is introduced into the generally U-shaped inflatable region portion. Conditioned air may also be introduced into a said inner inflatable region, before or after the inner blanket portion is at least partially (or fully) detached from the first inflatable region.

Preferably, the temperature of the temperature conditioned gas is regulated. The temperature conditioned gas may be temperature conditioned air. The temperature conditioned gas may be heated air. The humidity of the temperature conditioned gas may be controlled.

DESCRIPTION OF THE DRAWINGS

An example embodiment of the present invention will now be illustrated with reference to the following Figures in which.

DETAILED DESCRIPTION OF AN EXAMPLE EMBODIMENT

Figure 1:
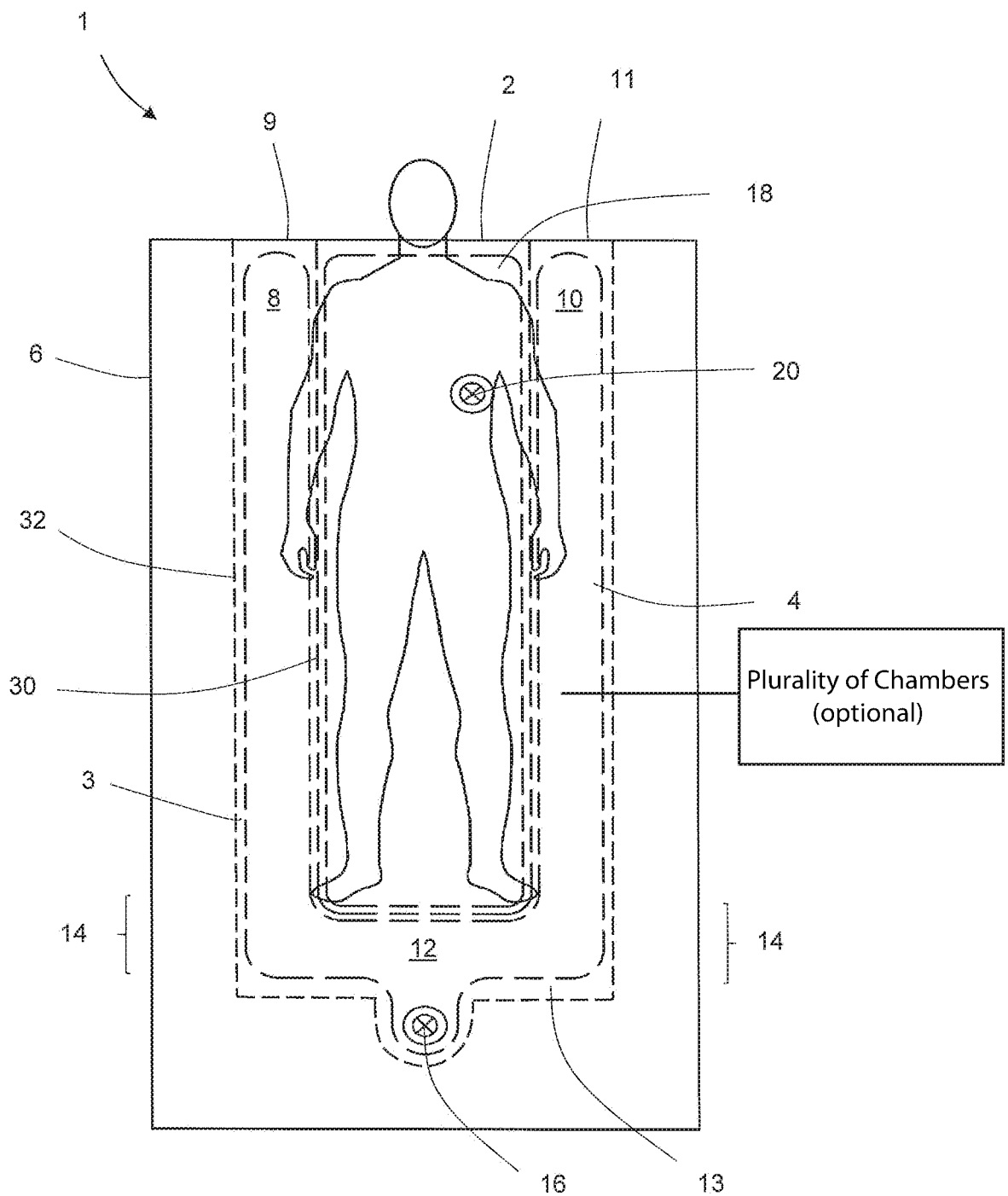
FIG. 1 is a plan view of an embodiment of the invention.

With reference to FIGS. 1 to 8, a forced air warming blanket 1, comprises an inner detachable blanket 2 (acting as an inner blanket portion), an intermediate blanket portion 3 (acting as the first blanket portion) having a generally U-shaped inflatable region 4 extending around three sides of the inner detachable blanket, and an outer detachable blanket 6 (acting as an outer blanket portion). The inflatable region comprises a first tube portion 8 within one arm 9 of the intermediate blanket portion (functioning as the first elongate portion), a second tube portion 10 within an opposite arm 11 of the intermediate blanket portion (functioning as the second elongate portion) and a tubular cross piece 12, with a connecting portion 13 of the intermediate blanket portion connecting the first tube portion and the second tube portion at one extremity 14 of the first and second tube portion 1, to form a general U-shaped blanket portion. The cross piece comprises an inlet 16 (acting as an inlet port) to allow temperature conditioned air to pass into the generally U-shaped inflatable region.

The inner detachable blanket comprises an inflatable chamber 18 (acting as the inner inflatable region), and an inlet 20 (acting as the inlet port of the inner blanket portion) through which temperature conditioned gas can be introduced into the chamber. The inner detachable blanket is bounded on three sides by the U-shaped inner edge 34 of the intermediate blanket portion.

The outer detachable blanket extends from the tube and forms the periphery of the forced air warming blanket. In the example of FIG. 1, the outer detachable blanket is not inflatable. When the forced air warming blanket is used under a patient, the outer detachable blanket can be tucked under a bed, or a mattress. When the forced air warming blanket is used above a patient, the outer detachable blanket retains conditioned air between itself and the bed upon which the patient is lying upon. In this way the outer detachable blanket extends the reach of the air flow of the forced air warming blanket.

The forced air warming blanket comprises a first, air-impermeable, sheet 24 and a second, air-permeable, sheet 26. During manufacture, the first and second sheets are connected by a plurality of heat seals 28 to form the generally U-shaped inflatable region, and the inner inflatable region. The second sheet therefore forms air-permeable regions of the generally U-shaped inflatable region and the inner inflatable chamber.

The first and second layers of the forced air warming blanket are perforated to form tear lines 30 where the inner detachable blanket connects to the intermediate detachable blanket, and to form further tear lines 32 where the outer detachable blanket connects to the intermediate detachable blanket, such that the inner detachable blanket and/or the outer detachable blanket may be separated from the intermediate detachable blanket by ripping the perforated first and second layers along the tear lines.

With reference to FIG. 1, in one application, the forced air warming blanket is placed over the body of a patient with air permeable sheet underneath, facing the patient. The head of the patient extends from one end of the forced air warming blanket, and the body of the patient is substantially surrounded by the tube of the forced air warming blanket. As such, the first and second tube portions extend alongside the body of the patient and the cross piece is located adjacent to the feet of the patient. Accordingly, the inner detachable blanket covers the body of the patient.

A first hose (not shown) is attached to the inlet of the cross piece and temperature conditioned air is forced with the tube through the first hose by a blower, temperature conditioned air passes out through the second, air-permeable, layer of the tube to the body of the subject, warming them.

Optionally, the inner detachable blanket may be inflated too, and used as a source of conditioned air to the subject by attaching a second hose to the inlet of the inner detachable blanket and forcing conditioned air into the inner inflatable region of the detachable blanket, again using a blower.

Figure 2:
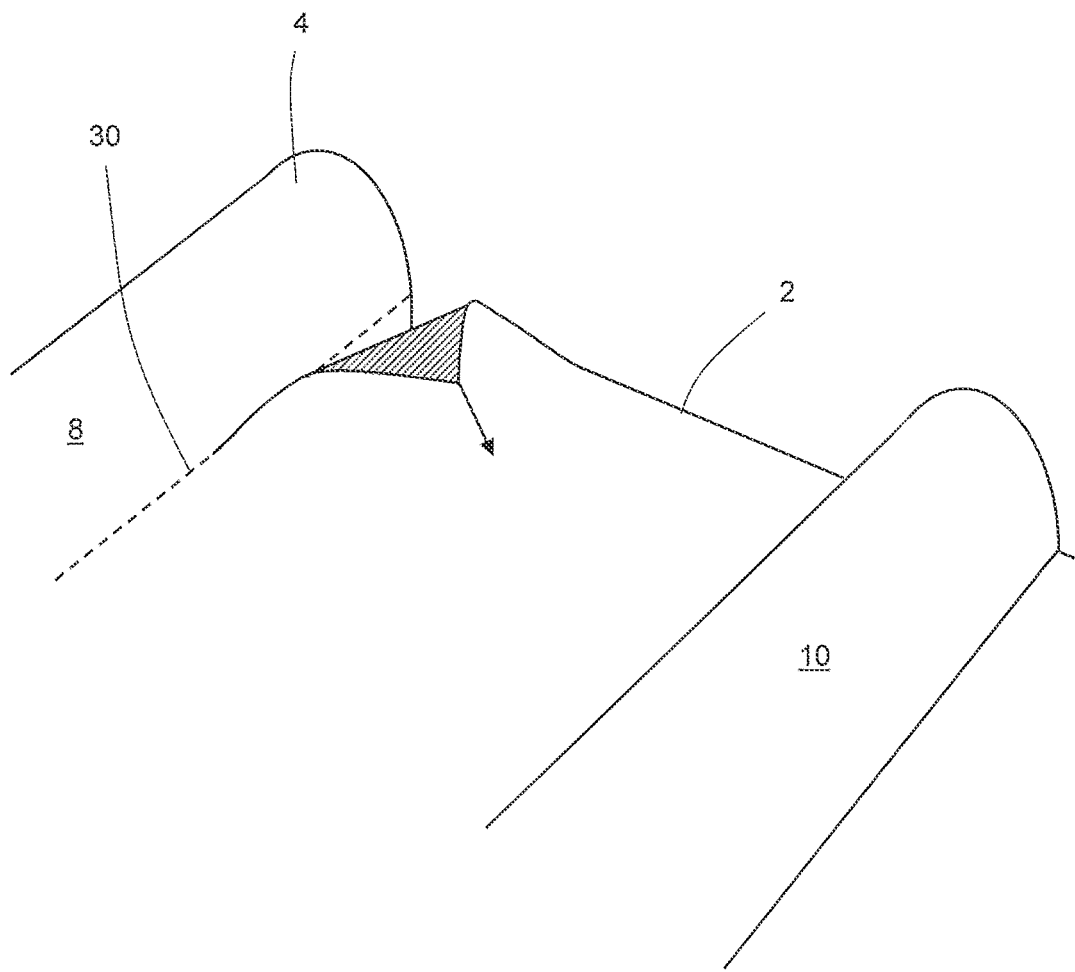
FIG. 2 is perspective view of a portion of an embodiment of the invention.
Figure 3:
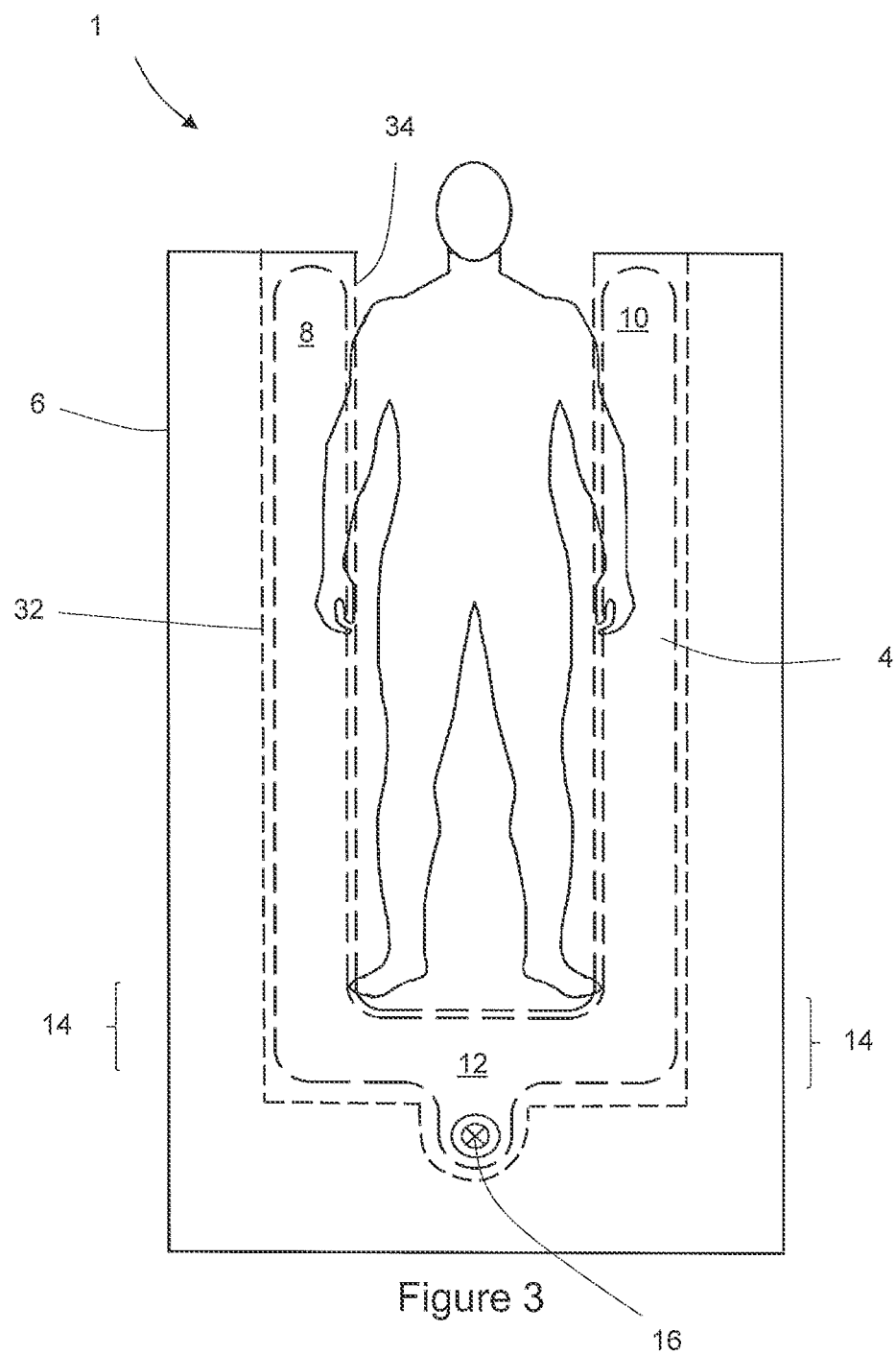
FIG. 3 is a plan view of an embodiment of the invention.

Whilst the forced air warming blanket is in use, if access to the body of the patient is required, the inner detachable blanket may be partially or entirely removed to expose the relevant area of the patient's body by ripping tear line 30. With reference to FIGS. 2 and 3, if access to the entirety of the patient's body is required, the inner detachable blanket can be partially or wholly removed, for example at one end, or down one side to enable access to the subject or to vary the amount of warming by allowing some conditioned air to escape.

As such, the forced air warming blanket can be adapted in use to ensure the body of a patient using the blanket is maintained at a constant temperature, whilst allowing the accessibility of the body to be changed as required.

Figure 4A:
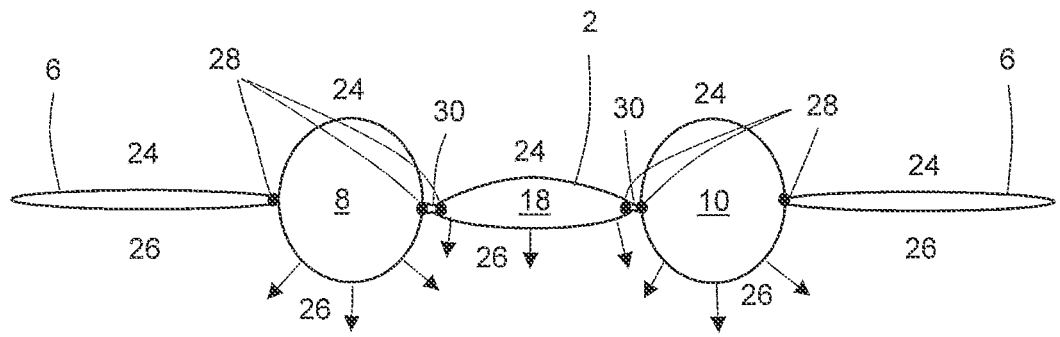
FIG. 4 is a section view through (a) an embodiment of the invention where both the first blanket portion and the inner blanket portion convey air to the body of a patient (b) an embodiment of the invention where the first blanket portion conveys air to the body of a patient.
Figure 4B:
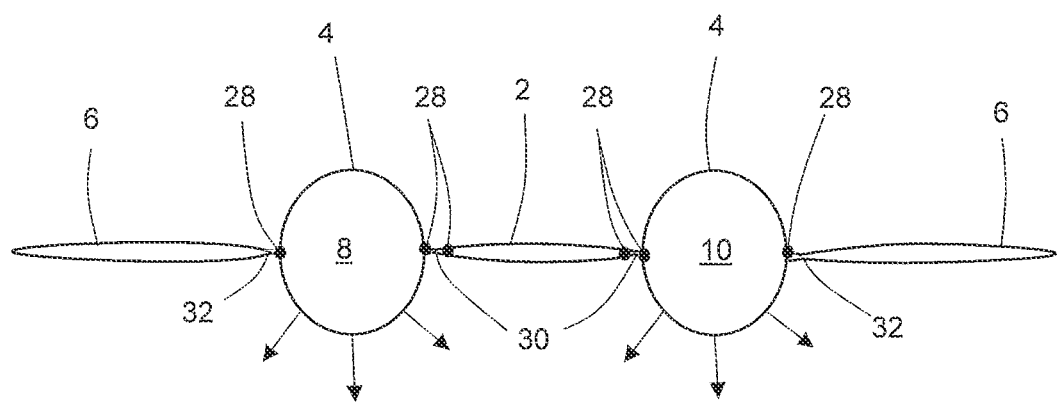
Figure 5:
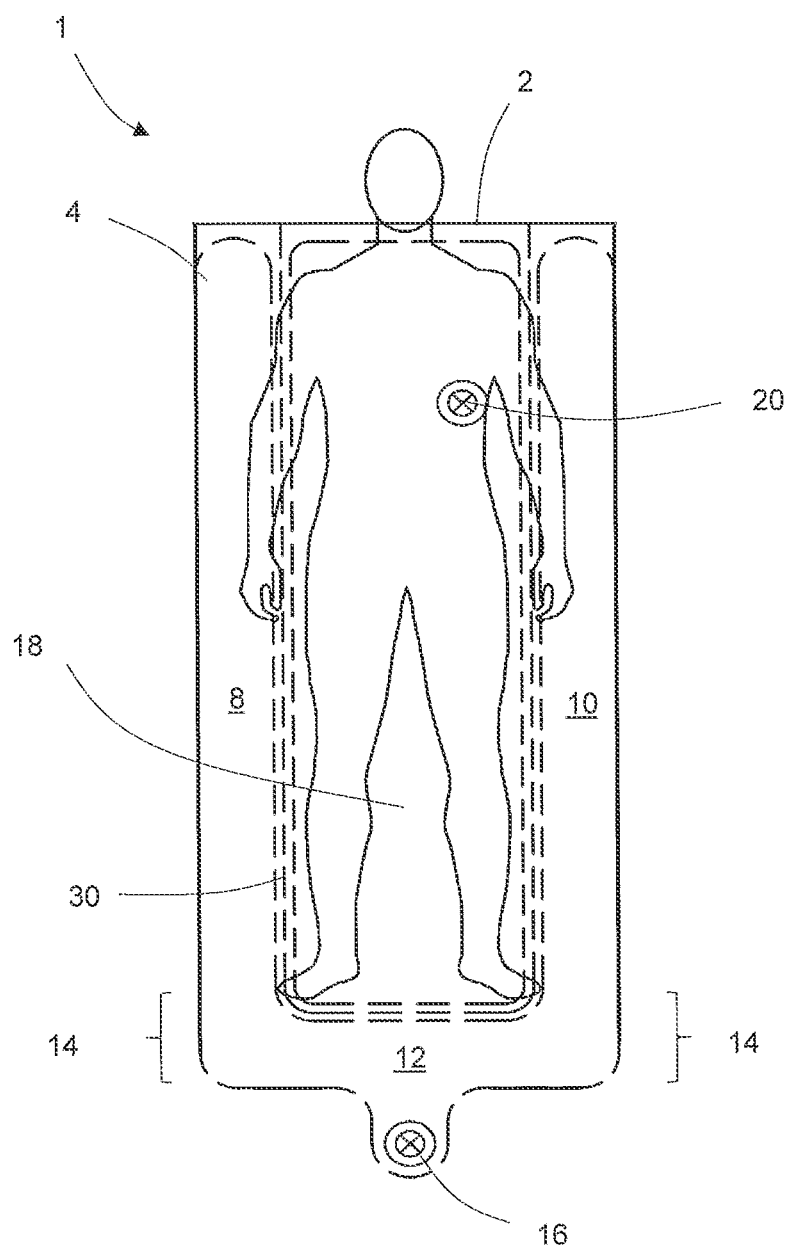
FIG. 5 is a plan view of an embodiment of the invention.
Figure 6:
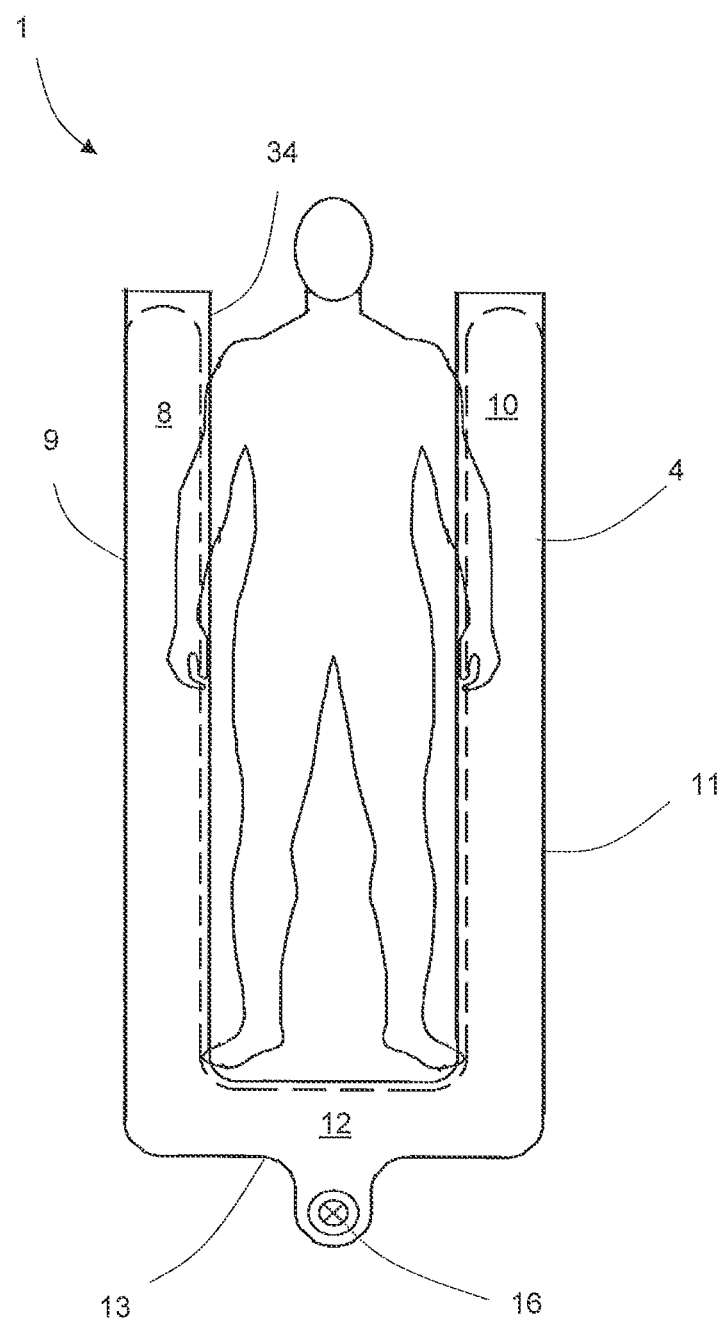
FIG. 6 is a plan view of an embodiment of the invention.

FIG. 4a shows the forced air warming blanket with the inner detachable blanket inflated and attached to the intermediate blanket portion and FIG. 4b corresponds except that the inner detachable blanket portion is deflated. Accordingly, the inner detachable blanket may be used independently as a forced air warming blanket, either while partially or fully attached to the intermediate blanket portion or after separation from the intermediate blanket portion. In this mode of use, the other detachable blanket assists by distributing conditioned air blown through the second sheet of the tube and/or inner detachable blanket.

Figure 8:
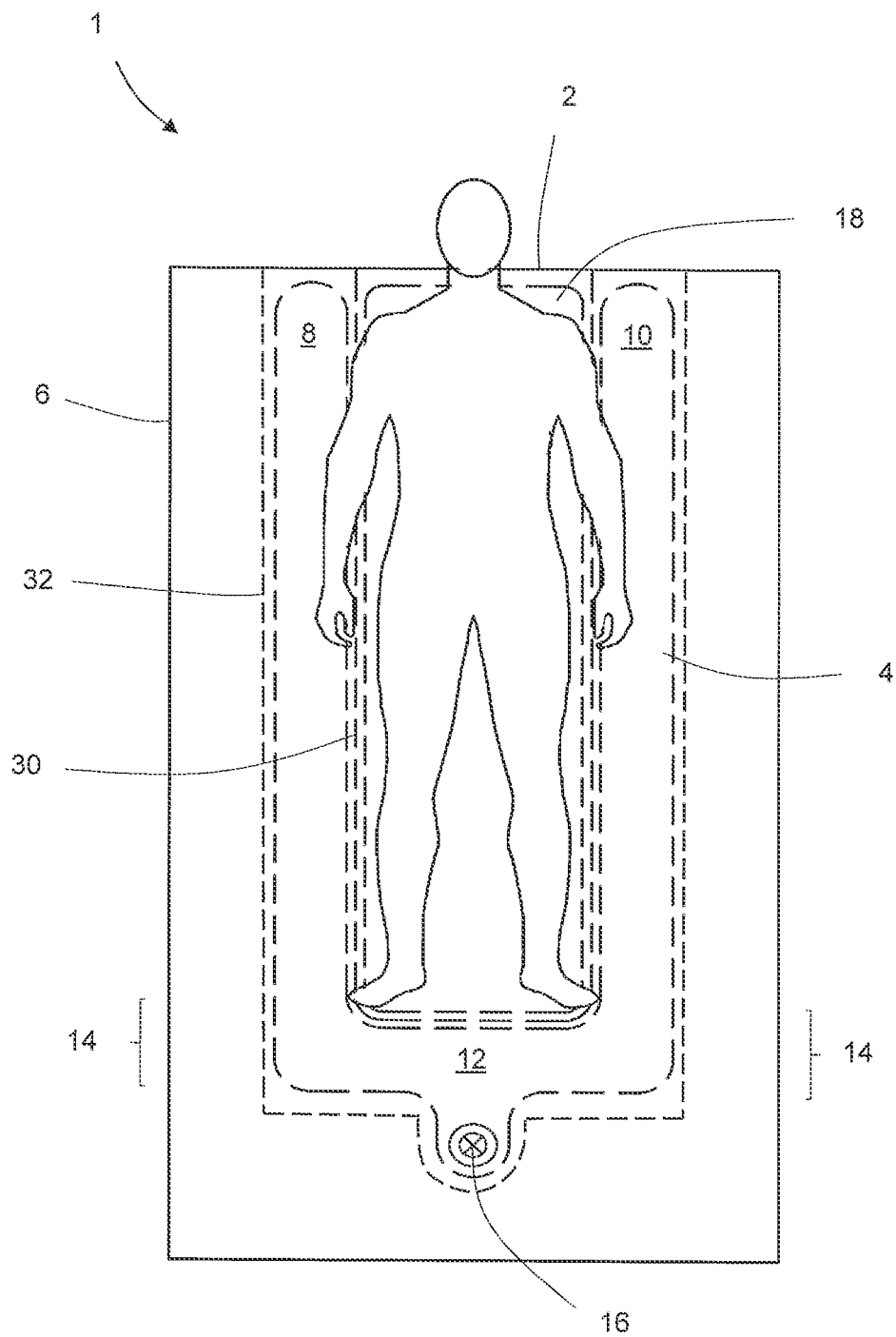
FIG. 8 is a plan view of an embodiment of the invention.

In a further alternative application, with reference to FIG. 8, the forced air warming blanket is used under the patient. That is, the patient lies on the forced air warming blanket and conditioned air is conveyed to the underside of the patient. The first, air-impermeable, layer is arranged away from the patient and the second, air-permeable, layer is arranged against the patient. Accordingly, this embodiment of the invention can be used both above and below a patient.

Either or both of the sheets which define the forced air warming blanket may have more than one layer, for example, the first air impermeable sheet may comprise a non-fabric layer and a metallic reflecting layer between the first and second layers. The air-permeable (second) sheet may comprise an inner layer and an outer layer, where the inner layer has greater resistance to the flow of air to thereby distribute air across the second sheet.

Figure 7:
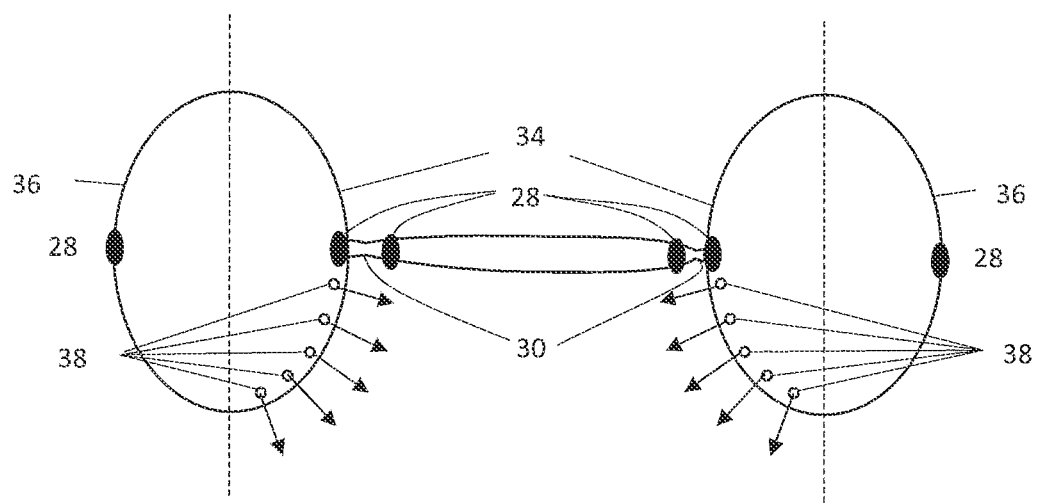
FIG. 7 is a cross section of an embodiment of the invention.

The product can be formed using alternative constructions, for example, with reference to FIG. 7, in an alternative embodiment, instead of being formed from a sheet of air permeable material and a sheet of air impermeable material, the inflatable region is formed from a sheet of material which is air impermeable (except where it is perforated) having an inner wall 34 and an outer wall 36. However, the inner wall comprises perforations 38 in the air impermeable sheet to make the inner wall air permeable and allow conditioned air to be conveyed from within the tube to the body of the patient. The perforations in the inner wall ensure that the majority of conditioned air is directed towards the body of the patient, and not towards the periphery of the forced air warming blanket.

In an alternative embodiment, the inner blanket portion is not fully detachable. The tear lines may be such that it will remain connected to the outer blanket portion, at least in part.

The outer blanket portion, where provided, could be formed from a different material. It need not be a continuation of the first and second sheets. It may be that one of the first and second sheets, but not the other, extends outside of the tube to form the outer blanket portion. Similarly, the inner blanket portion could be formed from a different material to the intermediate blanket portion. Again, it may be that one of the first and second sheets, but not the other, extends inside the intermediate blanket portion to form the inner blanket portion.

The outer blanket portion may also include an inflatable region and an air inlet. In some embodiments, the forced air warming blanket does not comprise an outer blanket portion, and the tube forms the periphery of the forced air warming blanket. Furthermore, where an outer blanket portion is present, it need not be detachable.

Further variations and modifications may be made within the scope of the invention herein disclosed.

The invention claimed is:

1. A forced air warming blanket configured to provide conditioned gas to a subject, the forced air warming blanket comprising:
    an inner blanket portion, comprising:
        an inner inflatable region having, at least, an external surface, wherein at least part of the external surface of the inner inflatable region is air permeable, and
        a first inlet port configured to receive temperature conditioned gas into the inner inflatable region;
    an intermediate blanket portion positioned outside of the inner blanket portion and having an external surface and a generally U-shaped inflatable region, wherein at least a part of the external surface of the generally U-shaped inflatable region is air permeable, and the generally U-shaped inflatable region further comprising a second inlet port configured to receive temperature conditioned gas;
    an outer blanket portion at least part of which is laterally outside the generally U-shaped inflatable region of the intermediate blanket portion; and
    first tear lines positioned between the inner blanket portion and the intermediate blanket portion; and
    second tear lines positioned between the intermediate blanket portion and the outer blanket portion, wherein the intermediate blanket portion and the inner blanket portion are detachable from the forced air warming blanket via the first tear lines, and the intermediate blanket portion and the outer blanket portion are detachable from the forced air warming blanket via the second tear lines.

2. The forced air warming blanket according to claim 1, wherein the intermediate blanket portion has a generally U-shaped inner edge, bounding the inner blanket portion on at least three sides.

3. The forced air warming blanket according to claim 1, wherein the inner blanket portion is entirely detachable from the intermediate blanket portion.

4. The forced air warming blanket according to claim 1, wherein the outer blanket portion comprises an outer inflatable region having an external surface, at least part of the external surface is air permeable, and an inlet port for receiving temperature conditioned gas into the outer inflatable region.

5. The forced air warming blanket according to claim 1, comprising opposed first and second sheets, wherein the first sheet is air impermeable and the second sheet is air permeable, and one or more seals which connect the first and second sheets and thereby define the generally U-shaped inflatable region.

6. The forced air warming blanket according to claim 5, wherein the inner blanket portion is also formed from the opposed first and second sheets.

7. The forced air warming blanket according to claim 5, wherein the second sheet is multi-laminar.

8. The forced air warming blanket according to claim 1, wherein the generally U-shaped inflatable region comprises a first tube portion and an opposed second tube portion with a cross piece therebetween, and the second inlet port is part of the cross piece of the generally U-shaped inflatable region.

9. A method of manufacturing a forced air warming blanket according to claim 1, the method comprising the steps of:
    bringing a first sheet of an air-impermeable material and a second sheet of an air-permeable material into contact, and;
    forming one or more seals between the first sheet and the second sheet and forming one or more tear lines through the first and second sheets to thereby form a forced air warming blanket.

10. A method of using a forced air warming blanket according to claim 1, comprising arranging the forced air warming blanket above or under a subject, introducing conditioned air into the generally U-shaped inflatable region through the second inlet port of the generally U-shaped inflatable region, and at least partially detaching the inner blanket portion.

11. The method of using a forced air warming blanket according to claim 10, whether the inner blanket portion is at least partially detached or fully detached before, after or while conditioned air is introduced into the generally U-shaped inflatable region and wherein temperature conditioned air is also introduced into a said inner inflatable region, before or after the inner blanket portion is at least partially detached or fully detached from the intermediate blanket portion.

12. The forced air warming blanket according to claim 1, wherein the first tear lines are configured so that complete detachment of the inner blanket portion from the intermediate blanket portion results in an opening through a blanket interior to the generally U-shaped inflatable region.

13. The forced air warming blanket according to claim 1, wherein
    at least part of the external surface of the inflatable region comprises perforations; and the perforations are configured to direct the temperature conditioned gas in a lateral direction into a space between upright legs of the U-shaped inflatable region.

14. The forced air warming blanket according to claim 1, wherein the outer blanket portion is not inflatable.

15. The forced air warming blanket according to claim 1, wherein the intermediate blanket portion and the inner blanket portion are independently inflatable.

16. The forced air warming blanket according to claim 1, wherein the generally U-shaped inflatable region is configured to at least partially retain temperature conditioned gas between an exterior of the generally U-shaped inflatable region and a subject that is interior to the generally U-shaped inflatable region.

17. The forced air warming blanket according to claim 1, wherein the first tear lines are configured to be torn in a range from partially detaching to fully detaching the inner blanket portion from the intermediate blanket portion.

18. A forced air warming blanket configured to provide conditioned gas to a subject, the forced air warming blanket comprising:
a first blanket portion which comprises a generally U-shaped inflatable region, at least part of an external surface of the generally U-shaped inflatable region being air permeable, the generally U-shaped inflatable region further comprising a first inlet port configured to receive temperature conditioned gas;
an inner blanket portion within the generally U-shaped inflatable region, the inner blanket portion comprising an inner inflatable region that is not in fluid communication with the inflatable region, at least part of an external surface of the inner blanket is air permeable, and a second inlet port configured to receive temperature conditioned gas into the inner inflatable region; and
first tear lines positioned between the inner blanket portion and the first blanket portion,
wherein the generally U-shaped inflatable region extends the full length of the blanket and is configured to extend from the subject's shoulders to feet, and
the first blanket portion and the inner blanket portion are detachable from the forced air warming blanket via the first tear lines.

* * * * *